United States Patent [19]

Wiechert et al.

[11] Patent Number: 4,892,867
[45] Date of Patent: Jan. 9, 1990

[54] ANTIANDROGENIC 17-ALPHA-ALKYL STEROIDS

[75] Inventors: Rudolf Wiechert; Dieter Bittler; Annerose Schleusener; Manfred Albring, all of Berlin, Fed. Rep. of Germany

[73] Assignee: Schering Aktiengesellschaft, Berlin and Bergkamen, Fed. Rep. of Germany

[21] Appl. No.: 918,231

[22] Filed: Oct. 14, 1986

Related U.S. Application Data

[60] Continuation of Ser. No. 784,121, Oct. 4, 1985, abandoned, which is a division of Ser. No. 620,216, Jun. 13, 1984, Pat. No. 4,558,041, which is a division of Ser. No. 380,328, May 20, 1982, Pat. No. 4,456,600, which is a division of Ser. No. 198,383, Oct. 30, 1980, Pat. No. 4,344,941.

[30] Foreign Application Priority Data

Oct. 26, 1979 [DE] Fed. Rep. of Germany ....... 2943776

[51] Int. Cl.$^4$ .......................... A61K 31/56; C07J 1/00
[52] U.S. Cl. .................... 514/178; 514/182; 260/397.4; 260/397.5
[58] Field of Search .............. 514/178, 182; 260/397.4, 397.5

[56] References Cited

U.S. PATENT DOCUMENTS 3,391,168  7/1968  Counsell et al. ................ 260/397.5
3,705,180 12/1972  Klimstra ........................ 260/397.4
4,344,941  8/1982  Wiechert et al. ............... 260/397.4
4,456,600  6/1984  Wiechert et al. ............... 260/397.4
4,558,041 12/1985  Wiechert et al. ............... 260/397.4

Primary Examiner—Douglas W. Robinson
Assistant Examiner—Joseph A. Lipovsky
Attorney, Agent, or Firm—Millen, White & Zelano

[57] ABSTRACT

17α-Alkyl steroids of the formula

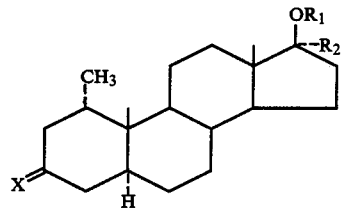

wherein
$R_1$ is hydrogen, acyl, alkyl, alkenyl, alkyl or alkenyl interrupted by an oxygen atom, cyclopentyl, or tetrahydropyranyl,
$R_2$ is alkyl or alkenyl of 2-6 carbon atoms,
X is oxygen or the grouping $H(OR_3)$ wherein $R_3$ is hydrogen, acyl, alkyl, alkenyl, alkyl or alkenyl interrupted by an oxygen atom, cyclopentyl, or tetrahydropyranyl, upon topical application, display antiandrogenic properties and can be utilized for the treatment of acne, seborrhea, alopecia and hirsutism.

22 Claims, No Drawings

ANTIANDROGENIC 17-ALPHA-ALKYL STEROIDS

This is a continuation, of application Ser. No. 784,121, filed 10/04/85, now abandoned, which is a div. of Ser. No. 620,216, filed 06/13/84, now U.S. Pat. No. 4,558,041, which is a div. of Ser. No. 380,328, filed 05/20/82, now U.S. Pat. No. 4,456,600, which is a div. of Ser. No. 198,383, filed 10/20/80, now U.S. Pat. No. 4,344,941.

BACKGROUND OF THE INVENTION

The present invention relates to new antiandrogenic steroids.

The compound of formula I below wherein $R_1$ and $R_2$ are hydrogen and X is oxygen, known as "mesterolone" is a strongly orally effective androgen. Mesterolone (1-αmethylandrostan- 17β-ol-3-one) is described, for example, in German Patent No. 1,152,100 and in "Arzneimittel-Forsch." [Drug Research] 16, 4 : 455–466 (1966).

SUMMARY OF THE INVENTION

It is an object of this invention to provide new steroids having valuable pharmacological properties.

Upon further study of the specification and appended claims, further objects and advantages of this invention will become apparent to those skilled in the art.

These objects have been attained in one aspect of this invention by providing 17α-substituted steroids of formula (I)

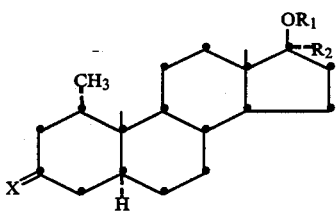

wherein
- $R_1$ is hydrogen, acyl, alkyl, alkenyl, alkyl or alkenyl interrupted by an oxygen atom, cyclopentyl or tetrahydropyranyl,
- $R_2$ is alkyl or alkenyl of 2–6 carbon atoms,
- X is oxygen or the grouping $H(OR_3)$ wherein $R_3$ is hydrogen, acyl, alkyl, alkenyl, alkyl or alkenyl interrupted by an oxygen atom, cyclopentyl or tetrahydropyranyl.

DETAILED DISCUSSION

The steroids of this invention contain an alkyl or alkenyl group $R_2$ in the 17α-position. Such groups include those of 2–6 carbon atoms, preferably those which are straight chained. Suitable groups $R_2$ include, for example, ethyl, propyl, butyl, pentyl and hexyl, propenyl etc. Branched groups include those such as isobutyl and isobutenyl.

The steroids of formula I contain a free, esterified or etherified hydroxy group ($OR_1$ or $OR_3$) in the 17α- and optionally also in the 3α- or 3α-position.

The esters $OR_1$ and $OR_3$ are derived from the acids customary in steroid chemistry. (See, e.g., U.S. Pat. No. 4,011,314). whose disclosure is incorporated by reference herein). Examples include organic carboxylic and sulfonic acids of 1–17 carbon atoms generally of a hydrocarbon nature, or equivalently, a substituted hydrocarbon nature; preferably utilized are organic carboxylic acids of 1–7 carbon atoms. Examples of suitable acyl groups $R_1$ and $R_3$ include formyl, acetyl, propionyl, butyryl, isobutyryl, caproyl, heptanoyl, chloroacetyl, trifluoroacetyl, glycoloyl, succinyl, glutaryl, adipoyl, dimethylaminopropionyl, benzoyl, nicotinoyl, isonicotinoyl, etc.

The ethers $OR_1$ and $OR_3$ contain an alkyl, alkenyl, cyclopentyl or tetrahydropyranyl group. Alkyl or alkenyl groups $R_1$ and $R_3$ preferably contain 1–5 carbon atoms and optionally are interrupted by an oxygen atom. Examples of such $R_1$ and $R_3$ groups include methyl, ethyl, methoxymethyl, methoxyethyl, ethoxyethyl, propyl, butyl, pentyl, etc.

The steroids of formula I can be prepared by reacting a 17-keto steroid of formula II

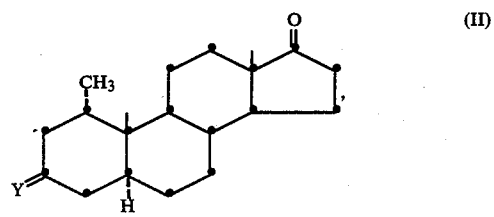

wherein Y is an acid-hydrolyzable, blocked 3-oxo group, with an $R_2$ organometallic compound to form the corresponding 17α-$R_2$ steroid; splitting off the blocking group in the 3-position; and, depending on the particularly desired form of $R_1$ and X in the final product, optionally esterifying or etherifying the 17-hydroxy group prior to or after the blocking group splitting-off step; and/or reducing the 3-keto group and/or, optionally, subsequently esterifying or etherifying free hydroxy groups in the 3-position or in the 3- and 17-positions.

This process is conducted using fully conventional reactions and procedures. For reacting the 17-keto group with an organometal compound yielding the residue $R_2$, the keto group must be blocked in the 3-position. The blocking group Y is to be cleavable by acidic hydrolysis. In a preferred embodiment, the keto group in the 3-position is blocked by ketal formation. The ketal residues Y are derived from the alcohols and thioalcohols usually employed for protecting free oxo groups. Examples include: ethylene glycol, 2,2-dimethyl-1,3-propanediol, and 1,2-ethanedithiol, etc. However, the 3-keto group can also be protected by enolether, enol ester, or enamine formation.

The reaction of the 17-keto compound of formula II can be conducted using with an organometallic compound ($R_2$-metal), especially with $R_2$-lithium, e.g. n-butyllithium, using conventional methods. The organometallic compound can also be produced in the reaction solution from the haloalkane and the alkali metal, such as, for example, 1-bromopentane or 1-bromohexane and lithium. The reaction is conducted in an inert solvent, e.g. ether, tetrahydrofuran, hexane, etc. The reaction temperature is 0° to 50° C., preferably room temperature.

To produce the 17α-propyl compound ($R_2$=propyl), the 17α-allyl compound is preferably formed-first of all by Grignardization with allylmagnesium bromide, and this compound is subsequently hydrogenated to the 17α-propyl compound. Hydrogenation takes place with catalytically activated hydrogen. Examples of suitable catalysts include palladium on carbon in methanol or tris(triphenyl) phosphine rhodium chloride in acetone. Analogously, the 17α-isobutyl compound is prepared by way of the 17α-isobutenyl compound.

The 17α-ethyl compound ($R_2$=ethyl) can be produced, for example, also in a manner known per se by way of the 17α-ethynyl compound. For this purpose, the 17-keto compound of formula II is converted, for example with ethynylmagnesium bromide or lithium acetylide, into the 17α-ethynyl compound, and the latter is then hydrogenated to the 17α-ethyl compound.

The 3-keto blocking group (Y) is split off, either before or optionally also after the possible esterification or etherification of the 17-hydroxy group, in accordance with methods known to those skilled in the art by means of acidic hydrolysis. To split off the blocking groups, suitable agents include mineral acids, e.g. perchloric acid, sulfuric acid, hydrochloric acid, or organic acids, such as, for example, oxalic acid. The splitting step is preferably effected in an alcoholic solution or in other polar solvents, e.g. acetone, at temperatures of about 20° to 100° C.

The processes customarily utilized in steroid chemistry for the esterification of tertiary steroid alcohols can serve for the optionally following esterification of the tertiary 17-hydroxy group, e.g. reaction with acids or acid anhydrides in the presence of strong acids, e.g. trifluoroacetic acid or p-toluenesulfonic acid, at temperatures of about 10° to 50° C., or the reaction with an acid anhydride in the presence of a tertiary amine, e.g. pyridine or collidine, at about 20° to 200° C. If pyridine and 4-(dimethylamino) pyridine are used together as the tertiary amines, the esterification of the teriary 17-hydroxy group can also be conducted at room temperature.

Alkylating compounds, such as, for example, alkyl halogenides, can be used for the etherification of the 17-hydroxy group or the hydroxy groups in the 3- or in the 3-and 17-positions. The etherification takes place conventionally in the presence of a strong base, such as sodium hydroxide solution, using a polar solvent, such as hexamethylphosphoric triamide, at 0°-50° C. or in the presence of a strong base, such as sodium hydride, with the use of an ether, such as tetrahydrofuran, at 30°-100° C.

For the preparation of alkyl ethers, the carbon chain of which is interrupted by an oxygen atom and optionally closed to a ring, the hydroxy compounds are converted with dihydropyran or alkyl vinyl ethers in the presence of a strong acid, such as p-toluenesulfonic acid or phosphorus oxychloride, into the corresponding tetrahydropyranyl or alkoxyethyl ethers. The reaction is preferably carried out in the presence of inert solvents, such as chloroform, dichloromethane, tetrahydrofuran, dioxane, etc., at a reaction temperature of −20° to 100° C. For the production of methoxymethyl ethers, the hydroxy compound is reacted, for example, with formaldehyde dimethylacetal in anhydrous dichloromethane in the presence of phosphorus pentoxide at room temperature.

The reduction of the keto group in the 3-position can be conducted according to known methods by hydrogenation with a metal hydride. Especially suitable hydrogen donors proved to be complex hydrides, e.g. sodium borohydride and lithium tri-(tert-butoxy) aluminum hydride. The reduction of sodium borohydride is preferably accomplished in an aqueousalcoholic solution, and the reduction with lithium tri-(tert-butoxy)-aluminum hydride is carried out in an ether solution. The reduction is effected under gentle conditions, preferably at temperatures of about 0° to 50° C.

An example for the subsequent esterification of the hydroxy group in the 3-position is the reaction with an acid anhydride or halogenide in the presence of a tertiary amine, such as, for example, pyridine, collidine, or triethylamine, at room temperature. The 3-hydroxy group can also be esterified with the acid anhydride with the use of a strong acid, such as p-toluenesulfonic acid, or with the corresponding acid and trifluoroacetic anhydride at room temperature.

When conducting the esterification in the presence of an acidic catalyst at room temperature or in the presence of an alkaline catalyst at an elevated temperature of 20°-200° C., the hydroxy groups in the 3- and 17-position can also be esterified simultaneously.

If pyridine and 4-(dimethylamino) pyridine are used together as the alkaline catalysts, then both hydroxy groups can also be esterified in an alkaline medium at room temperature.

The starting material 17-keto steroids of formula II can be produced according to methods known per se from 1α-methyl-5α-androstan-17β-ol-3-one by the introduction of a blocking group in the 3-position and oxidation in the 17-position. The preparation of compounds of formula II is explained below in greater detail, using as an example the production of 3,3-ethylenedioxy-1α-methyl-5α-androstan-17-one:

20 g of 17β-hydroxy-1α-methyl-5α-androstan-3-one is stirred under reflux with the use of a water trap in 500 ml of benzene with 60 ml of ethylene glycol and 600 mg of p-toluenesulfonic acid for 5.5 hours. After cooling, the reaction solution is diluted with ether, washed with sodium bicarbonate solution and water, and dried. Yield after evaporation: 23 g of crude 3,3-ethylenedioxy-1α-methyl-5α-androstan-17β-ol.

23 g of 3,3-ethylenedioxy-1α-methyl-5α-androstan-17β-ol is agitated for 1 hour at room temperature in 230 ml of dichloromethane with 20 g of pyridinium chlorochromate in the presence of 20 g of sodium acetate. The reaction solution is then diluted with ether, filtered off from the insoluble proportions, and the filtrate is washed with water. After drying and evaporation, 21.5 g of 3,3-ethylenedioxy-1-methyl-5α-androstan-17-one is obtained as the crude product.

It has now been found that the 17α-alkyl steroids of formula I derived from mesterolone show antiandrogenic properties upon topical administration. These 17α-alkyl steroids counteract androgens which are present or administered. Thus, using the compounds of formula I, the growth of the flank organs and the sebaceous glands of the ears, stimulated by testosterone propionate, is inhibited in castrated male hamsters. On the other hand, other androgen-dependent organs, such as prostate and seminal vesicles are not significantly affected.

The topical antiandrogenic effect was determined as follows.

Male fertile hamsters weighing about 80 grams are castrated and 0.1 mg of testosterone propionate is subcutaneously administered daily as a substitute. The right ear and the right flank organ are treated twice daily with 0.01 ml of a 3% solution of the antiandrogen to be tested in an organic solvent, preferably acetone, over a period of 3 weeks. On the 22nd day, the animals are killed with ether; the prostate, seminal vesicles and lumbar organs are prepared and weighed, the ears are processed histologically, and the areas of the sebaceous glands are measured. Using the ears of other treated animals, the incorporation of $^{14}C$-labeled glucose into the lipids of the sebaceous glands is measured.

It has been found that the sebaceous gland conglomerates, as the size of the flank organs and the sebaceous glands at the ventral sides of the ear lobes of the hamster, which latter glands can be well distinguished and readily detected planimetrically, are dependent on androgen. As a parameter for the sebaceous gland function, the incorporation of $^{14}C$-labeled precursors in lipid synthesis is measured.

By comparing the areas of the sebaceous glands, the weights of the flank organs, and the lipogenesis of the side respectively treated with the antiandrogen, along with solvent control, a measure is obtained for the local effect of the antiandrogen.

For topical application, to mammals, e.g., humans, the 17α-alkyl steroids of this invention can be processed with conventional excipients into solutions, suspensions, gels, ointments, creams, powders or other preparations. Suitable excipients include, for example, water, ethanol, propanol, glycerin, methylcellulose, hydroxypropylcellulose, carboxypolymethylene, etc. The antiandrogen is preferably used in a concentration of 0.05–5.0% by weight, based on the total weight of the preparation. The preparations can be utilized for the topical treatment of diseases such as acne, seborrhea, alopecia and hirsutism analogously to the use of the known topical agent Topterone (U.S. Pat. No. 4,039,669) e.g., by administration 1–3 times a day to the affected area.

In an experiment, the right flank organ and the right ear of castrated Syrian golden hamsters were topically treated for 21 days twice daily with 0.01 ml of a 3% ethanolic solution of 17β-hydroxy-1α-methyl-17α-n-propyl-5α-androstan-3-one (A). The golden hamsters were furthermore treated daily with 0.1 mg of testosterone propionate in benzyl benzoate/castor oil in a ratio of 1:100 via subcutaneous administration. On the 22nd day, the animals were sacrificed; seminal vesicles, prostates, and flank organs were prepared and weighed, and the area sizes of the sebaceous glands of the histologically further processed ears were measured. Ten animals were used per experiment.

The results are shown in the following table:

|  | Seminal Vesicles mg | Prostate mg | Flank Organs mg | | Areas mm$^2$ | |
|---|---|---|---|---|---|---|
|  |  |  | Right | Left | Right | Left |
| A | 1101 ± 34.58 | 355 ± 21.91 | 35 ± 1.92 | 67 ± 3.64 | 0.0634 ± 0.0054 | 0.1516 ± 0.021 |
| Control | 1106 ± 46.52 | 404 ± 23.82 | 70 ± 3.53 | 72 ± 3.67 | 0.2309 ± 0.026 | 0.2428 ± 0.023 |

A marked reduction in weight of the treated right-hand flank organ and a reduction of the sebaceous gland size (area) of the treated right ear are determined. With local application of A, the seminal vesicle weight is affected hardly at all, and the prostate weight is only slightly influenced.

In another experiment, the sebum production of the sebaceous glands of hamster ears treated as above was measured by incorporation of ($^{14}C$) sodium acetate into the lipids of the sebaceous gland cells in vitro and subsequent determination of radioactivity in the lipid extract. The average values and the standard deviations were calculated from the radioactivity of the individual specimens. The percentage inhibition of lipogenesis of the treated right ears was calculated as compared with the control group, i.e. the right ears treated with the solvent. This experiment revealed a marked and dose-dependent reduction of lipogenesis in the treated ears.

| A (%) | Reduction of Lipogenesis (%) |
|---|---|
| 3 | 43.8 ± 7.0 |
| 1 | 51.9 ± 7.6 |
| 0.3 | 26.25 ± 21.0 |
| 0.1 | 33.6 ± 14.0 |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

800 mg of magnesium filings are reacted in 20 ml of absolute ether with 2 ml of allyl bromide in 5 ml of absolute ether to obtain allylmagnesium bromide. At room temperature 2 g of 3,3-ethylenedioxy-1α-methyl-5α-androstan-17-one in 5 ml of dichloromethane is added to this solution, and the latter is agitated for 3 hours. The ice-cooled reaction solution is then gradually combined with saturated ammonium chloride solution, diluted with ether, washed with saturated ammonium chloride solution and water, yielding, after drying and evaporation, 2.1 g of 3,3-ethylenedioxy-1α-methyl-17α-(2-propenyl)-5α-androstan-17β- ol as a crude product.

2.1 g of 3,3-ethylenedioxy-1α-methyl-17α-(2-propenyl)-5α-androstan-17β-ol is hydrogenated in 105 ml of methanol with 210 mg of palladium on charcoal (10%) until one equivalent of hydrogen has been absorbed. The catalyst is filtered off and the filtrate evaporated under vacuum, yielding 2.1 g of 3,3-ethylenedioxy-1α-methyl-17α-n-propyl-5α-androstan-17β-ol as a crude product. A sample recrystallized from diisopropyl ether melts at 150°–150.5° C.

1.5 g of 3,3-ethylenedioxy-1α-methyl-17α-n-propyl-5α-androstan-17β-ol is stirred at room temperature in 30 ml of methanol and 3 ml of water with 1.5 g of oxalic acid for 2 hours. The mixture is then diluted with ether, washed with water, and dried. After evaporation the residue is chromatographed on silica gel, producing 1.1 g of 17β-hydroxy-1α-methyl-17α-n-propyl-5α-androstan-3-one as an oil.

$[\alpha]_D^{23} = +7.5°$ (chloroform).

EXAMPLE 2

1.25 g of 3,3-ethylenedioxy-1α-methyl-5α-androstan-17-one is combined in 12.5 ml of absolute tetrahydrofuran, under ice cooling and passing argon over the mixture, with 3.5 ml of a butyllithium solution (15% in hexane) and stirred for 22 hours at room temperature. The excess reagent is then decomposed with water, the reaction solution is diluted with ether and washed with water. After drying and evaporation the residue is chromatographed on silica gel, thus obtaining 950 mg of 17α-n-butyl-3,3-ethylenedioxy-1α-methyl-5α-androstan-17β-ol as a crude product.

950 mg of 17α-n-butyl-3,3-ethylenedioxy-1α-methyl-5α-androstan-17β-ol is stirred in 10 ml of methanol with 1 ml of 8 vol-% sulfuric acid for 30 minutes at room temperature. The mixture is diluted with ether, washed with water, and dried. The residue obtained after evaporation is chromatographed on silica gel, thus producing 620 mg of 17α-n-butyl-17β-hydroxy-1α-methyl-5α-androstan-3-one as an oil.

$[\alpha]_D^{23} = +5.6°$ (chloroform).

EXAMPLE 3

Under pressure, 400 mg of lithium is introduced into 20 ml of ice-cooled absolute tetrahydrofuran, and then 7.8 ml of 1-bromopentane is added dropwise. After the reaction is finished, 1.6 g of 3,3-ethylenedioxy-1α-methyl-5α-androstan-17-one, dissolved in 8 ml of absolute tetrahydrofuran, is added thereto. The mixture is agitated for 48 hours at room temperature under argon and then worked up as described in Example 2. Chromatography on silica gel yields 1.1 g of 3,3-ethylenedioxy-1α-methyl-17α-n-pentyl-5α-androstan-17β-ol as an oil.

1.0 g of 3,3-ethylenedioxy-1α-methyl-17α-n-pentyl-5α-androstan-17β-ol is used for ketal splitting as in Example 2 and then worked up. After chromatography on silica gel, 720 mg of 17β-hydroxy-1α-methyl-17α-n-pentyl-5α-androstan-3-one is obtained as an oil.

$[\alpha]_D^{23} = +4°$ (chloroform).

EXAMPLE 4

500 mg of lithium is introduced under pressure into 30 ml of ice-cooled, absolute tetrahydrofuran and then 11.3 ml of 1-bromohexane is added dropwise. After the reaction is finished, 2.0 g of 3,3-ethylenedioxy-1α-methyl-5α-androstan-17-one in 10 ml of absolute tetrahydrofuran is added dropwise to the mixture, and the latter is stirred under argon for 48 hours at room temperature. The mixture is worked up as described in Example 2 and chromatographed on silica gel, yielding 950 mg of 3,3-ethylenedioxy-17α-n-hexyl-1α-methyl-5α-androstan-17β-ol as an oil.

850 mg of 3,3-ethylenedioxy-17α-n-hexyl-1α-methyl-5α-androstan-17β-ol is reacted under ketal-splitting conditions as in Example 2 and then worked up. After chromatography on silica gel, 630 mg of 17α-n-hexyl-17β-hydroxy-1α-methyl-5α-androstan-3-one is obtained as an oil.

$[\alpha]_D^{23} = +4°$ (chloroform).

EXAMPLE 5

1.5 g of magnesium filings is reacted in 40 ml of absolute tetrahydrofuran with 4.9 ml of ethyl bromide to obtain ethylmagnesium bromide. This solution is added dropwise under ice cooling to 40 ml of absolute tetrahydrofuran, through which acetylene is conducted. 3 g of 3,3-ethylenedioxy-1α-methyl-5α-androstan-17-one is added to the acetylenemagnesium bromide solution, and the mixture is stirred for 23 hours at room temperature. Under ice cooling the excess reagent is then decomposed with saturated ammonium chloride solution, then diluted with ether, and washed with water. After drying and evaporation the residue is chromatographed on silica gel, thus obtaining 2.65 g of 17α-ethynyl-3,3-ethylenedioxy-1α-methyl-5α-androstan-17β-ol as a crude product.

1.4 g of 17α-ethynyl-3,3-ethylenedioxy-1α-methyl-5α-androstan-17β-ol is hydrogenated in 70 ml of methanol with 200 mg of palladium on charcoal (5%) until 2 equivalents of hydrogen has been absorbed. The mixture is then filtered off from the catalyst and evaporated under vacuum, yielding 1.4 g of 17α-ethyl-3,3-ethylenedioxy-1α-methyl-5α-androstan-17β-ol as an oil.

1.4 g of 17α-ethyl-3,3-ethylenedioxy-1α-methyl-5α-androstan-17β-ol is used for ketal splitting as described in Example 2 and worked up. After chromatography on silica gel and recrystallization from diisopropyl ether, 1.1 g of 17α-ethyl-17β-hydroxy-1α-methyl-5α-androstan-3-one is obtained, m.p. 151.5°-152.5° C.

EXAMPLE 6

5.0 g of 17β-hydroxy-1α-methyl-17α-n-propyl-5α-androstan-3-one is stirred in 5 ml of absolute tetrahydrofuran with 5.0 g of lithium tri-tert.-butoxyaluminum hydride for 3 hours at room temperature. The mixture is diluted with ether, washed with dilute sulfuric acid and water, dried, and evaporated. After chromatography on silica gel and respective recrystallization from diisopropyl ether, 860 mg of 1α-methyl-17α-n-propyl-5α-androstane-3β,17β-diol, m.p. 117°-118° C., and 3.3 g of 3α-isomer, m.p. 143°-144° C., are obtained.

EXAMPLE 7

1.5 g of 17β-hydroxy-1α-methyl-17α-n-propyl-5α-androstan-3-one is allowed to stand at room temperature in 6 ml of pyridine with 3 ml of acetic anhydride for 16 hours, after the addition of 75 mg of 4-dimethylaminopyridine. After the mixture has been precipitated into ice water and recrystallized from hexane, 1.3 g of 17β-acetoxy-1α-methyl-17α-n-propyl-5α-androstan-3-one is obtained, m.p. 128°-129° C.

EXAMPLE 8

1.0 g of 17β-acetoxy-1α-methyl-17α-n-propyl-5α-androstan-3-one is reacted as described in Example 6 with lithium tri-tert.-butoxyaluminum hydride and worked up. After chromatography on silica gel, 650 mg of 17β-acetoxy-1α-methyl-17α-n-propyl-5α-androstan-3β-ol is obtained as an oil.

EXAMPLE 9

250 mg of 17β-acetoxy-1α-methyl-17α-n-propyl-5α-androstan-3β-ol is allowed to stand at room temperature for 48 hours in 1 ml of pyridine with 0.5 ml of butyric anhydride. The mixture is diluted with ether, washed repeatedly with water, dried, and evaporated. The residue is chromatographed on silica gel, yielding 270 mg of 17β-acetoxy-3β-butyryloxy-1α-methyl-17α-n-propyl-5α-androstane as an oil.

EXAMPLE 10

400 mg of 17β-acetoxy-1α-methyl-17α-n-propyl-5α-androstan-3β-ol is combined in 2.8 ml of absolute dichloromethane and 1.8 ml of formaldehyde dimethylacetal with a mixture of 600 mg of kieselguhr W 20 and 300 mg of phosphorus pentoxide and stirred for 45 minutes at room temperature. The mixture is vacuum-filtered from the insoluble components and washed with dichloromethane containing 3-5% triethylamine. The crude product obtained after evaporation is chromatographed on silica gel, thus producing 280 mg of 17β-acetoxy-3β-methoxymethoxy-1α-methyl-17α-n-propyl-5α-androstane.

EXAMPLE 11

400 mg of 17β-hydroxy-1α-methyl-17α-n-propyl-5α-androstan-3-one is stirred for 42 hours at room temperature in 1.6 ml of pyridine and 0.8 ml of enanthic anhydride with the addition of 40 mg of 4-dimethylaminopyridine. The mixture is diluted with ether, washed with water, dried, and evaporated. The residue is chromatographed on silica gel, yielding 370 mg of 17β-heptanoyloxy-1α-methyl-17α-n-propyl-5α-androstan-3-one as an oil.

EXAMPLE 12

7.0 g of 3,3-ethylenedioxy-1α-methyl-5α-androstan-17-one is combined in 70 ml of tetrahydrofuran with 2.8 g of magnesium filings; 14.35 ml of crotyl bromide in 15 ml of tetrahydrofuran is then gradually added dropwise to the reaction mixture and the latter is stirred for 45 minutes at room temperature. The excess reagent is decomposed under ice cooling with ammonium chloride solution; then the reaction solution is diluted with ether, washed with water, dried, and evaporated. The residue is chromatographed on silica gel, thus obtaining 1.95 g of 3,3-ethylenedioxy-1α-methyl-17α-(1-methyl-2-propenyl)-5α-androstan-17β-ol as a crude product.

1.92 g of 3,3-ethylenedioxy-1α-methyl-17α-(1-methyl-2-propenyl)-5α-androstan-17α-ol is stirred in 19.2 ml of methanol with 1.92 ml of 8 vol-% sulfuric acid for 15 minutes at room temperature. The mixture is then diluted with ether, washed neutral with water, dried, and evaporated. The residue is chromatographed on silica gel. Recrystallization from diisopropyl ether yields 780 mg of 17β-hydroxy-1α-methyl-17α-(1-methyl-2-propenyl)-5α-androstan-3-one, m.p. 148.5°-150° C.

770 mg of 17β-hydroxy-1α-methyl-17α-(1-methyl-2-propenyl)-5α-androstan-3 -one is hydrogenated in 5 ml of tetrahydrofuran and 15 ml of methanol with 150 mg of palladium on charcoal (10%) until one equivalent of hydrogen has been absorbed. The catalyst is filtered off and the filtrate evaporated under vacuum. The residue is chromatographed on silica gel. Recrystallization from diisopropyl ether yields 440 mg of 17β-hydroxy-1α-methyl-17α-(1-methyl-n-propenyl)-5α-androstan-3-one, m.p. 172.5°-173.5° C.

EXAMPLE 13

700 mg of 1α-methyl-17α-n-propyl-5α-androstane-3α,17β-diol (prepared according to Example 6, m.p. 143°-144° C.) is allowed to stand at room temperature for 22 hours in 2.8 ml of pyridine and 1.4 ml of acetic anhydride. After ice water precipitation, the thus-obtained crude product is chromatographed on silica gel, yielding 760 mg of 3α-acetoxy-1α-methyl-17α-n-propyl-5α-androstan-17β-ol as an oil.

EXAMPLE 14

1.5 g of 1α-methyl-17α-n-propyl-5α-androstane-3α,17β-diol is allowed to stand in 6 ml of triethylamine and 1.5 ml of acetic anhydride with 50 mg of 4-dimethylaminopyridine for 6 days at room temperature. After ice water precipitation, the thus-produced crude compound is chromatographed on silica gel, yielding 1.08 g of 3α,17β-diacetoxy-1α-methyl-17α-n-propyl-5α-androstane, m.p. 96°-99° C.

EXAMPLE 15

One gram of 3,3-ethylenedioxy-1α-methyl-17α-(2-propenyl)-5α-androstan-17β-ol (prepared according to Example 1) is stirred in 10 ml of methanol with 1 ml of 8 vol-% sulfuric acid for 15 minutes at room temperature and then worked up analogously to Example 12. Recrystallization from diisopropyl ether yields 710 mg of 17β-hydroxy-1α-methyl-17α-(2-propenyl)-5α-androstan-3-one, m.p. 115°-116° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 17α-substituted steroid of the formula

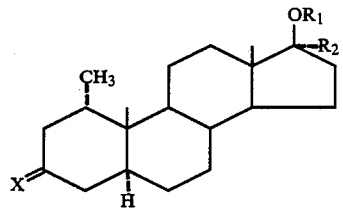

wherein
$R_1$ is hydrogen, an acyl group of a $C_{1-17}$ hydrocarbon carboxylic or sulfonic acid, $C_{1-5}$ alkyl, $C_{1-5}$-alkenyl, $C_{1-5}$-alkyl or $C_{1-5}$-alkenyl interrupted by an oxa atom, cyclopentyl or tetrahydropyranyl,
$R_2$ is $C_{3-4}$-alkyl, and
X is oxygen or H(OR$_3$) wherein $R_3$ is hydrogen, an acyl group of a $C_{1-17}$ hydrocarbon carboxylic or sulfonic acid, $C_{1-5}$ alkyl, $C_{1-5}$-alkenyl, cyclopentyl or tetrahydropyranyl.

2. 17β-Hydroxy-1α-methyl-17α-n-propyl-5α-androstan-3-one, a compound of claim 1.

3. 17α-n-Butyl-17β-hydroxy-1α-methyl-5α-androstan-3-one, a compound of claim 1.

4. 1α-Methyl-17α-n-propyl-5α-androstane-3β,17β-diol, a compound of claim 1.

5. 17β-Acetoxy-1α-methyl-17α-n-propyl-5α-androstan-3-one, a compound of claim 1.

6. 17β-Acetoxy-1α-methyl-17α-n-propyl-5α-androstan-3β-ol, a compound of claim 1.

7. 17β-Acetoxy-3β-butyryloxy-1α-methyl-17α-n-propyl-5α-androstane, a compound of claim 1.

8. 17β-Heptanoyloxy-1α-methyl-17α-n-propyl-5α-androstan-3-one, a compound of claim 1.

9. 1α-Methyl-17α-n-propyl-5α-androstane-3α,17β-diol, a compound of claim 1.

10. 3α,17β-Diacetoxy-1α-methyl-17α-n-propyl-5α-androstane, a compound of claim 1.

11. A compound of claim 1 wherein $R_1$ is $C_{1-5}$ alkyl, $C_{1-5}$ alkenyl, $C_{1-5}$-alkyl or $C_{1-5}$-alkenyl interrupted by an oxa atom, cyclopentyl or tetrahydropyranyl.

12. A compound of claim 1 wherein $R_1$ is an acyl group of a $C_{1-17}$ optionally substituted, hydrocarbon carboxylic or sulfonic acid.

13. A compound of claim 12 wherein $R_1$ is chloroacetyl, glycoloyl, trifluoroacetyl, succinyl, glutaryl, adipoyl, benzoyl, dimethylaminopropionyl, nicotinoyl or isonicotinoyl.

14. A compound of claim 13 wherein X is $OR_3$ wherein $R_3$ is an acyl group of a $C_{1-17}$ hydrocarbon carboxylic or sulfonic acid, $C_{1-5}$ alkyl, $C_{1-5}$-alkenyl, cyclopentyl or tetrahydropyranyl.

15. A compound of claim 1 wherein $R_1$ is H.

16. A compound of claim 15 wherein X is $OR_3$ wherein $R_3$ is an acyl group of a $C_{1-17}$ hydrocarbon carboxylic or sulfonic acid, $C_{1-5}$ alkyl, $C_{1-5}$-alkenyl, cyclopentyl or tetrahydropyranyl.

17. A compound according to claim 1 wherein X is $H(OR_3)$ and $R_3$ is cyclopentyl or tetrahydropyranyl.

18. A compound according to claim 1 wherein $R_1$ is $C_{1-5}$-alkyl or $C_{1-5}$-alkenyl interrupted by an oxa-atom.

19. A compound according to claim 1 wherein $R_1$ is $C_{1-5}$-alkyl or $C_{1-5}$-alkenyl interrupted by an oxa-atom, cyclopentyl or tetrahydropyranyl.

20. A compound according to claim 1 wherein X is oxygen.

21. A pharmaceutical composition comprising an antiandrogenically topically effective amount of a compound of the formula

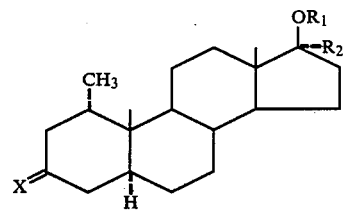

wherein
$R_1$ is hydrogen, an acyl group of a $C_{1-17}$ hydrocarbon carboxylic or sulfonic acid, $C_{1-5}$ alkyl, $C_{1-5}$-alkenyl, $C_{1-5}$-alkyl or $C_{1-5}$-alkenyl interrupted by an oxa atom, cyclopentyl or tetrahydropyranyl,
$R_2$ is $C_{3-4}$-alkyl, and
X is oxygen or $H(OR_3)$ wherein $R_3$ is hydrogen, an acyl group of a $C_{1-17}$ hydrocarbon carboxylic or sulfonic acid, $C_{1-5}$-alkyl, $C_{1-5}$-alkenyl, cyclopentyl or tetrahydropyranyl, and a pharmaceutically acceptable carrier for topical formulations.

22. A pharmaceutical composition comprising an antiandrogenically topically effective amount of a compound of the formula

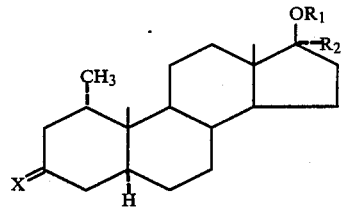

wherein
$R_1$ is hydrogen, an acyl group of a $C_{1-17}$ hydrocarbon carboxylic or sulfonic acid, $C_{1-5}$ alkyl, $C_{1-5}$-alkenyl, $C_{1-5}$-alkyl or $C_{1-5}$-alkenyl interrupted by an oxa atom, cyclopentyl or tetrahydropyranyl,
$R_2$ is $C_{3-4}$-alkyl, and
X is oxygen and a pharmaceutically acceptable carrier for topical formulations.

* * * * *